(12) United States Patent
Kakeya et al.

(10) Patent No.: US 11,986,530 B2
(45) Date of Patent: May 21, 2024

(54) DRUG COMPOSITION FOR PARENTERAL ADMINISTRATION

(71) Applicants: THERABIOPHARMA INC., Kawasaki (JP); KYOTO UNIVERSITY, Kyoto (JP)

(72) Inventors: Hideaki Kakeya, Kyoto (JP); Masashi Kanai, Kyoto (JP); Nobuaki Takahashi, Kyoto (JP); Tadashi Hashimoto, Meguro-ku (JP); Atsushi Imaizumi, Hino (JP); Hitomi Ozawa, Yokohama (JP)

(73) Assignees: THERABIOPHARMA INC., Kawasaki (JP); KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 16/858,810

(22) Filed: Apr. 27, 2020

(65) Prior Publication Data

US 2020/0254105 A1 Aug. 13, 2020

Related U.S. Application Data

(62) Division of application No. 16/313,252, filed as application No. PCT/JP2017/023753 on Jun. 28, 2017.

(30) Foreign Application Priority Data

Jun. 29, 2016 (JP) .................................. 2016-128889

(51) Int. Cl.
| | |
|---|---|
| A61K 47/54 | (2017.01) |
| A61K 9/00 | (2006.01) |
| A61K 31/12 | (2006.01) |
| A61K 31/185 | (2006.01) |
| A61K 31/223 | (2006.01) |
| A61K 31/7028 | (2006.01) |
| A61K 38/00 | (2006.01) |
| A61P 3/06 | (2006.01) |
| A61P 9/00 | (2006.01) |
| A61P 25/28 | (2006.01) |
| A61P 29/00 | (2006.01) |
| A61P 35/00 | (2006.01) |
| A61P 37/08 | (2006.01) |

(52) U.S. Cl.
CPC .......... *A61K 47/549* (2017.08); *A61K 9/0019* (2013.01); *A61K 31/12* (2013.01); *A61K 31/185* (2013.01); *A61K 31/223* (2013.01); *A61K 31/7028* (2013.01); *A61K 38/00* (2013.01); *A61P 3/06* (2018.01); *A61P 9/00* (2018.01); *A61P 25/28* (2018.01); *A61P 29/00* (2018.01); *A61P 35/00* (2018.01); *A61P 37/08* (2018.01)

(58) Field of Classification Search
CPC ..... A61K 47/549; A61K 31/12; A61K 31/185
See application file for complete search history.

(56) References Cited

U.S. PATENT DOCUMENTS

| | | | |
|---|---|---|---|
| 5,486,528 A | 1/1996 | Bajnogel et al. | |
| 2004/0037902 A1 | 2/2004 | Pandol et al. | |
| 2009/0131373 A1 | 5/2009 | Giori et al. | |
| 2010/0316631 A1* | 12/2010 | Safavy ............... | A61K 36/9066 |
| | | | 424/133.1 |

FOREIGN PATENT DOCUMENTS

| | | |
|---|---|---|
| CN | 101400360 A | 4/2009 |
| CN | 102552225 A | 7/2012 |
| CN | 105492011 A | 4/2016 |
| JP | 2011-107130 | 6/2011 |

OTHER PUBLICATIONS

Parvathy (Chemical Approaches toward preparation of water-soluble curcumin Derivatives; Thesis, 2009, 1-222).*
International Search Report dated Aug. 8, 2017 in PCT/JP2017/023753 filed on Jun. 28, 2017.
Thangavel, S. et al, "Redox nanoparticles inhibit curcumin oxidatice degradation and enhance its therapeutic effect on prostate cancer", Journal of Controlled Release, vol. 209. Apr. 22, 2015, pp. 110-119 (total 10 pages).
Sahu, A. et al., "Synthesis of novel biodegradable and self-assembling methoxy poly(ethylene glycol)—palmitate nanocarrier for curcumin delivery to cancer cells", Acta Biomaterialia, vol. 4, May 11, 2008, pp. 1752-1761 (total 10 pages).
Hui, S. et al., "Quantitative analysis of curcuminoids in human plasma by means of HPLC with UV detection", Clinical Chemistry, 2009, vol. 38, pp. 59-68 (with English summary) (total 10 pages).
Pal, A. et al., "Curcumin Glucuronides: Assessing the Proliferative Activity against Human Cell Lines", Bioorg Med Chem., Jan. 1, 2014, vol. 22, No. 1, pp. 435-439 (total 14 pages).
Shoji, M. et al., "Comparison of the effects of curcumin and curcumin glucuronide in human hepatocellular carcinoma HepG2 cells", Food Chemistry, 2014, vol. 151, pp. 126-132 (7 pages).
Combined Chinese Office Action and Search Report dated Jul. 3, 2020 in Chinese Patent Application No. 201780039599.1 (with unedited computer generated English translation and English translation of Category of Cited Documents), citing documents AO through AQ and AX therein, 17 pages.
Office Action dated Mar. 3, 2021 in Corresponding Chinese Patent Application No. 201780039599.1 (with machine translation) citing documents AA, AO, AP, AR, AS, AT, AU, AV, AW, AX and AY.
Pharmacology of Chinese Herbal Medicine, Edited by Gong Jiayu, Chinese Herbal Medicine Publisher, Aug. 31, 2002, p. 161.

(Continued)

*Primary Examiner* — Pancham Bakshi
(74) *Attorney, Agent, or Firm* — Oblon, McClelland, Maier & Neustadt, L.L.P.

(57) ABSTRACT

Provided is a curcumin pharmaceutical preparation that is highly water soluble, can maintain the concentration of free curcumin in the blood sufficiently high by being administered parenterally, can effectively obtain a pharmacological action of curcumin, and is highly safe.
A pharmaceutical composition for parenteral administration, including a water-soluble substance conjugate of curcumin as an active component.

1 Claim, 3 Drawing Sheets

(56) References Cited

OTHER PUBLICATIONS

Absorption, distribution, metabolism, excretory toxicity and drug efficacy of ingredients of Chinese herbal medicines (first volume), Edited by Yang Xiuwei, China Medical Science Press, Aug. 31, 2006, pp. 233-238 (with machine translation).

Hitomi Ozawa-Umeta, et al., "Curcumin β-D-glucuronide exhibits anti-tumor effects on oxaliplatin-resistant colon cancer with less toxicity in vivo", Cancer Science, vol. 111, Dec. 31, 2020, pp. 1785-1793.

Hossam M. M. Arafa, et al., "Possible contribution of β-glycosidases and caspases in the cytotoxicity of novel glycoconjugates in colon cancer cells", Investigational New Drugs vol. 28, May 5, 2009, pp. 306-317.

Anil Kumar, Utpal Bora et al., "In silico inhibition studies of NF-jB p50 subunit by curcumin and its natural derivatives", Medicinal Chemistry Research 21(10), Nov. 16, 2011, pp. 3281-3287.

Ashutosh Pal et al., "Curcumin glucuronides: Assessing the proliferative activity against human cell lines", Bioorganic&Medicinal Chemistry, vol. 22, Nov. 12, 2013, pp. 435-439.

Motomu Shoji et al., "Comparison of the effects of curcumin and curcumin glucuronide in human hepatocellular carcinoma HepG2 cells", Food Chemistry, vol. 151, Nov. 13, 2014, pp. 126-132.

Hitomi Ozawa, et al., "Curcumin β-D-Glucuronide Plays an Important Role to Keep High Levels of Free-Form Curcumin in the Blood", Biol. Pharm. Bull. vol. 40, No. 9, Dec. 31, 2017, pp. 1515-1524.

Office Action dated Jun. 10, 2021 in corresponding European Patent Application No. 17820211.5 with references AX and AY cited therein.

Erika Pfeiffer, et al., "Curcuminoids Form Reactive Glucuronides In Vitro",J. Agric. Food Chem. vol. 55, No. 2, Jan. 1, 2007, pp. 538-544.

Andrew G Kunihiro, "Site-Specific Deglucuronidation of Turmeric-Derived Curcuminoids in Bone", The FASEB Journal, vol. 30, No. S1, Apr. 1, 2016, p. 690.14.

Parvathy, K. S., "Chemical approaches toward preparation of water-soluble curcumin derivatives", Thesis, Dec. 31, 2009, pp. 1-222.

Hui, Quantitative analysis of curcuminoids in human plasma by means of HPLC with UV detection, 2009.

Nakagawa "British Journal of Nutrition (2014)", 112, pp. 8-14.

* cited by examiner

DRUG COMPOSITION FOR PARENTERAL ADMINISTRATION

This application is a divisional application of application Ser. No. 16/313,252, filed Dec. 26, 2018; which is a national stage application of PCT/JP2017/023753, filed Jun. 28, 2017; which claims priority to Japanese patent application 2016-128889, filed Jun. 29, 2016, the contents of these applications is incorporated herein by reference.

FIELD OF THE INVENTION

The present invention relates to a pharmaceutical composition for parenteral administration represented by intravenous administration.

BACKGROUND OF THE INVENTION

In recent years, it has been revealed that curcumin has a pharmacological action such as a tumor formation inhibitory action, an anti-oxidant action, an anti-inflammatory action, a cholesterol-lowering action, an anti-allergic action, a brain disease preventive action, and a heart disease preventive and therapeutic action, and it has been studied to use the curcumin, for example, for food (for example, functional food), pharmaceuticals, or cosmetics.

However, it is known that curcumin is hardly soluble in water, and therefore, is hardly absorbed in the body when orally ingested as it is. In addition, it is indicated that most of the curcumin that has been slightly absorbed by oral ingestion is present in the blood as a curcumin conjugate conjugated with glucuronic acid and/or sulfuric acid, and free form of curcumin is present only slightly in the blood (Non Patent Literature 1).

In general, it is well known that in a case where foreign substances are absorbed in the body, many of the foreign substances are inactivated by in vivo metabolism such as conjugation. In order to evaluate whether or not a curcumin conjugate has a pharmacological action, A. Pal, et al. investigated the cell growth inhibitory effect of a curcumin conjugate on KBM-5, Jurkat cells, U266 and A549 cell lines in vitro, and found that free curcumin has an effect of suppressing the growth of these cells (anti-cancer effect), while indicating that there is no such an effect with the curcumin conjugate (curcumin monoglucuronide and curcumin diglucuronide) (Non Patent Literature 2). In addition, when investigated the influence on the growth inhibitory effect of a curcumin conjugate on human hepatocellular carcinoma cell lines (HepG2 cells) and the gene expression, by oral administration, Shoji, et al. found the cell growth inhibitory effect with free curcumin, however, the effect was not found with the curcumin conjugate (curcumin monoglucuronide), and indicated that as to also the influence on the gene expression, the action was extremely low with the curcumin conjugate (curcumin monoglucuronide) as compared to that with free curcumin (Non Patent Literature 3). As described above, it is considered that curcumin is also conjugated, as a result of which a pharmacological action possessed by the curcumin is inactivated.

For this reason, in order to sufficiently obtain the expected pharmacological action of curcumin, it is required to sufficiently increase the concentration of free curcumin in the blood. However, due to the reasons described above, it is extremely difficult to increase the concentration of free curcumin in the blood even if curcumin is ingested orally.

Therefore, it is conceivable to administer curcumin parenterally into the body, however, since curcumin is hardly soluble in water, curcumin itself cannot be administered parenterally. For this reason, for example, a method in which a poorly water-soluble compound such as curcumin is subjected to a treatment for increasing the solubility, and then the obtained preparation is administered parenterally has been proposed (Patent Literatures 1 and 2).

PRIOR ART

Patent Literature

Patent Literature 1: JP 5-178765 A
Patent Literature 2: JP 2006-111534 A

Non Patent Literature

Non Patent Literature 1: Hui, et al., Clinical Chemistry, 2009, 38: 59-68
Non Patent Literature 2: A. Pal, et al., Bioorg Med Chem., 2014, 22(1), 435-439
Non Patent Literature 3: M. Shoji, et al., Food Chemistry, 2014, 151, 126-132

SUMMARY OF THE INVENTION

Problem to be Solved by the Invention

However, in order to obtain a curcumin aqueous solution by inclusion of curcumin with cyclodextrin, the amount of cyclodextrin is required to be 100 to 1000 times the amount of the curcumin (Patent Literature 2), and the curcumin aqueous solution was not usable for parenteral administration.

Therefore, an object of the present invention is to provide a curcumin preparation that is highly water soluble, can maintain the concentration of free curcumin in the blood sufficiently high by being administered parenterally, can effectively obtain a pharmacological action of curcumin, and is highly safe.

Means for Solving the Problem

Therefore, the present inventors have conducted intensive studies in order to solve the problem described above, it was found that when a water-soluble substance conjugate of curcumin is administered parenterally, surprisingly, the concentration of free curcumin in the blood can be maintained at a high level, and as a result, a pharmacological action possessed by curcumin can be sufficiently obtained. In addition, the curcumin conjugate contained in the pharmaceutical composition for parenteral administration is an in vivo metabolite of curcumin, and therefore, has extremely high safety.

That is, the present invention is to provide the following [1] to [20].

[1] A pharmaceutical composition for parenteral administration, including a water-soluble substance conjugate of curcumin as an active component.

[2] The pharmaceutical composition for parenteral administration according to [1], wherein the water-soluble substance is one or more kinds selected from glucuronic acid, sulfuric acid, glutathione, and amino acid.

[3] The pharmaceutical composition for parenteral administration according to [1] or [2], wherein the water-soluble substance is one or more kinds selected from glucuronic acid, and sulfuric acid.

[4] The pharmaceutical composition for parenteral administration according to anyone of [1] to [3], wherein the pharmaceutical composition for parenteral administration is a pharmaceutical composition selected from an anti-cancer agent, an anti-inflammatory agent, a cholesterol-lowering agent, an anti-allergic agent, a cognitive function improving agent, and a heart disease preventive and therapeutic agent.

[5] The pharmaceutical composition for parenteral administration according to any one of [1] to [4], wherein the pharmaceutical composition for parenteral administration is a pharmaceutical composition for intravenous administration.

[6] Use of a water-soluble substance conjugate of curcumin, for producing a pharmaceutical composition for parenteral administration.

[7] The use according to [6], wherein the water-soluble substance is one or more kinds selected from glucuronic acid, sulfuric acid, glutathione, and amino acid.

[8] The use according to [6] or [7], wherein the water-soluble substance is one or more kinds selected from glucuronic acid, and sulfuric acid.

[9] The use according to any one of [6] to [8], wherein the pharmaceutical composition for parenteral administration is a pharmaceutical composition for parenteral administration selected from an anti-cancer agent, an anti-inflammatory agent, a cholesterol-lowering agent, an anti-allergic agent, a cognitive function improving agent, and a heart disease preventive and therapeutic agent.

[10] The use according to any one of [6] to [9], wherein the use is for producing a pharmaceutical composition for intravenous administration.

[11] A water-soluble substance conjugate of curcumin, for use as a medicine for parenteral administration.

[12] The water-soluble substance conjugate according to [11], wherein the water-soluble substance is one or more kinds selected from glucuronic acid, sulfuric acid, glutathione, and amino acid.

[13] The water-soluble substance conjugate according to [11] or [12], wherein the water-soluble substance is one or more kinds selected from glucuronic acid, and sulfuric acid.

[14] The water-soluble substance conjugate according to any one of [11] to [13], wherein the medicine for parenteral administration is a medicine for parenteral administration selected from an anti-cancer agent, an anti-inflammatory agent, a cholesterol-lowering agent, an anti-allergic agent, a cognitive function improving agent, and a heart disease preventive and therapeutic agent.

[15] The water-soluble substance conjugate according to any one of [11] to [14], wherein the medicine for parenteral administration is a medicine for intravenous administration.

[16] A curcumin therapy, including parenterally administering a water-soluble substance conjugate of curcumin.

[17] The curcumin therapy according to [16], wherein the water-soluble substance is one or more kinds selected from glucuronic acid, sulfuric acid, glutathione, and amino acid.

[18] The curcumin therapy according to [16] or [17], wherein the water-soluble substance is one or more kinds selected from glucuronic acid, and sulfuric acid.

[19] The curcumin therapy according to any one of [16] to [18], wherein the curcumin therapy is a therapy selected from a cancer therapy, an anti-inflammatory therapy, a cholesterol-lowering therapy, an anti-allergic therapy, a cognitive function improving therapy, and a heart disease preventive therapy.

[20] The curcumin therapy according to any one of [16] to [19], wherein the parenteral administration is intravenous administration.

Effects of Invention

The pharmaceutical composition for parenteral administration according to the present invention, in which a water-soluble substance conjugate of curcumin is contained as an active component, can maintain the concentration of free curcumin in the blood at a high level for a long period of time by being administered parenterally, and as a result, a pharmacological action (for example, anti-tumor action) possessed by curcumin can be effectively obtained. In addition, the pharmaceutical composition for parenteral administration is a water-soluble substance conjugate of curcumin, which contains an in vivo metabolite of curcumin as an active component, and therefore, has extremely high safety.

DESCRIPTION OF EMBODIMENTS

Figure 1:
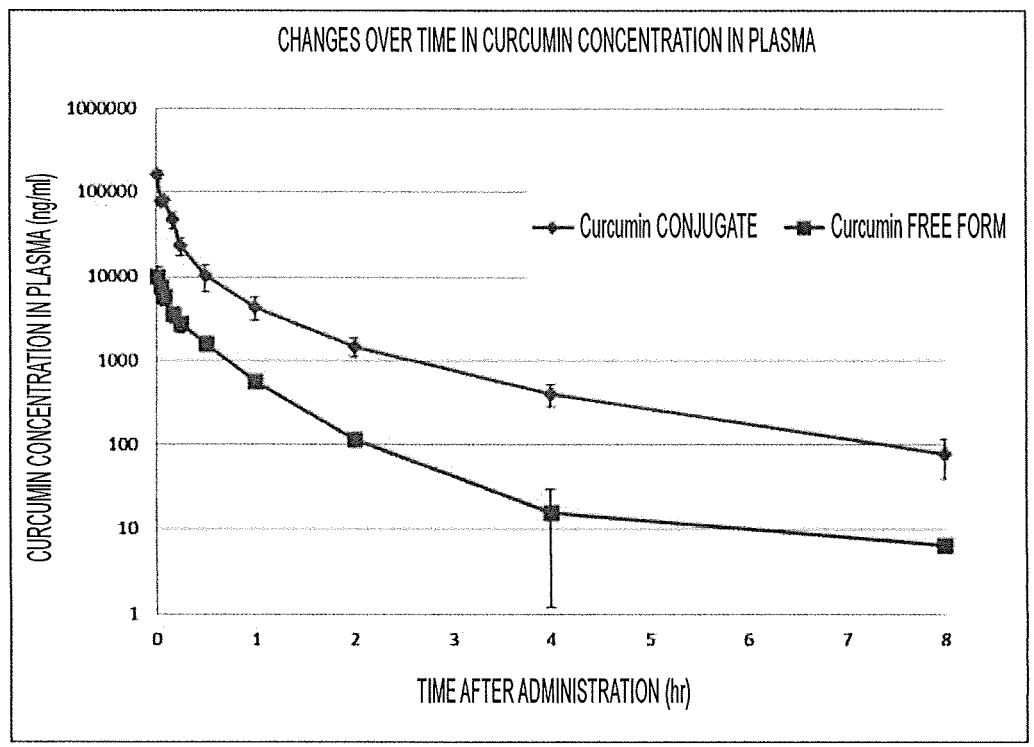
FIG. 1 shows the changes in concentration in blood of each of conjugate and free curcumin after intravenous administration of curcumin conjugates.

The pharmaceutical composition for parenteral administration according to the present invention contains a water-soluble substance conjugate of curcumin as an active component.

(A) Curcumin is a main component of the curcuminoid contained in turmeric pigment, and is a compound represented by the following structural formula (1).

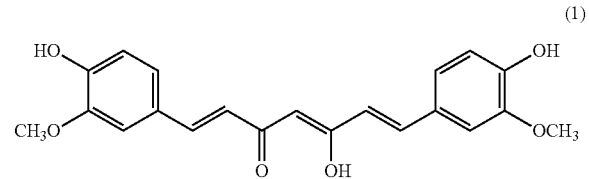

In the present invention, as the curcumin, chemically synthesized curcumin may be used, or curcumin distributed as turmeric pigment may be used. Examples of the turmeric pigment include powdered turmeric obtained by pulverizing a dried rhizome of *Curcuma longa* LINNE, crude curcumin or oleoresin (turmeric oleoresin) obtained by extracting the powdered turmeric with an appropriate solvent (for example, ethanol, fat and oil, propylene glycol, hexane, or acetone), and purified curcumin.

In addition, curcumin includes both of keto and enol forms of curcumin, which are tautomers.

As the water-soluble substance forming a conjugate with curcumin, a water-soluble substance usually present in a living body can be mentioned, and one or more kinds selected from glucuronic acid, sulfuric acid, glutathione and amino acid are preferred, and one or more kinds selected from glucuronic acid and sulfuric acid are more preferred.

Herein, as the amino acid, an amino acid present in a living body, for example, an essential amino acid can be mentioned.

The binding molar ratio of the curcumin in a curcumin conjugate to the water-soluble substance is preferably curcumin:water-soluble substance=1:1 to 1:3, more preferably curcumin:water-soluble substance=1:1 to 1:2, and furthermore preferably curcumin:water-soluble substance=1:1.

The conjugated form (binding form) of the curcumin and the water-soluble substance is, for example, a form of the following formula (2).

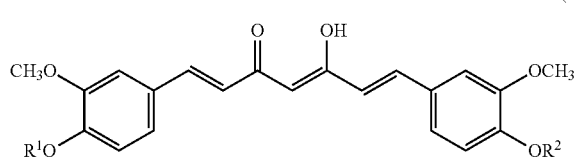

(2)

(in the formula, at least one of $R^1$ and $R^2$ is a residue of the water-soluble substance, and the remainder is a hydrogen atom.)

In the formula (2), one or both of $R^1$ and $R^2$ are preferably a glucuronic acid residue or a sulfuric acid residue, and the remainder is preferably a hydrogen atom.

A water-soluble substance conjugate of curcumin can be produced by the method described in Non Patent Literature 2 or 3.

The form of the pharmaceutical composition for parenteral administration containing a water-soluble substance conjugate of curcumin is not limited as long as it is administered parenterally, and in particular, a composition for injection (injection) is preferred. Examples of the composition for injection include a composition for intravenous administration, and a composition for subcutaneous administration, and a composition for intravenous administration is more preferred.

The content of the water-soluble substance of curcumin in the pharmaceutical composition for parenteral administration according to the present invention is not particularly limited, and is preferably 1 to 100% by mass, more preferably 5 to 100% by mass, and furthermore preferably 10 to 100% by mass.

In the composition for parenteral administration according to the present invention, in addition to the active components described above, for example, water, a saline solution, a pH adjusting agent, sugars, an acid, an alkali, a buffer agent, an isotonizing agent, a stabilizer, an analgesic, and an antiseptic agent can be mixed.

Herein, examples of the sugars include monosaccharides, disaccharides, trisaccharides, polysaccharides, and a sugar alcohol. Examples of the acid and the alkali include a water-soluble inorganic acid, a water-soluble inorganic acid salt, a water-soluble organic acid, a water-soluble organic acid salt, an amino acid, and an amino acid salt.

In addition, the form of the composition for parenteral administration according to the present invention may be a form of a powder filler (crystal or freeze-dried product) to be dissolved at the time of use, or may be a form of an aqueous solution.

As described in Examples later, the composition for parenteral administration according to the present invention can maintain the concentration in blood of free curcumin having a pharmacological action at a high level over a long period of time, for example, by being administered intravenously. In addition, the composition for parenteral administration exhibits an excellent pharmacological action (for example, anti-tumor effect) by being administered parenterally, for example, being administered intravenously, and therefore, is useful particularly as an anti-cancer agent, an anti-inflammatory agent, a cholesterol-lowering agent, an anti-allergic agent, a cognitive function improving agent, or a heart disease preventive and therapeutic agent, and in particular, is useful as an anti-cancer agent.

EXAMPLES

Next, the present invention will be described in more detail by way of Examples.

Production Example 1

(Preparation Method of Curcumin Conjugate (Curcumin Monoglucuronide))

(1) 1.0 g (2.52 mmol) of acetobromo-α-D-glucuronic acid methyl ester (compound a) and 326.0 mg (2.15 mmol) of vanillin (compound b) were dissolved in 8.7 mL of quinoline, and into the resultant mixture, 522.0 mg of silver oxide was added, then the mixture was stirred for 30 minutes while cooling in ice, and then the temperature of the mixture was raised to room temperature, and the resultant mixture was stirred for 90 minutes. After 26.0 mL of acetic acid was added into the resultant mixture, the mixture was transferred to 260.0 mL of distilled water, and subjected to celite filtration. The obtained water layer was subjected to extraction twice with ethyl acetate, an organic layer was combined together, and the resultant mixture was washed with brine and dried with $Na_2SO_4$, and the solvent was distilled off under reduced pressure. The obtained residue was purified with $SiO_2$ flash column chromatography (AcOEt/n-hexane=30:70, then 80:20), and 491.8 mg (49%) of a compound c was obtained.

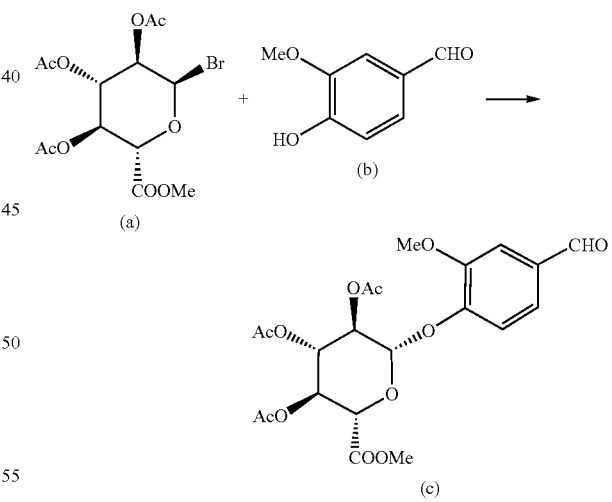

(2) 3.3 mL (32.07 mmol) of 2,4-pentanedione and 2.0 g (28.7 mmol) of diboron trioxide were dissolved in 30.0 mL of ethyl acetate, and the resultant mixture was stirred at 80° C. for 30 minutes. Into this resultant mixture, 2.2 g (14.4 mmol) of vanillin (compound b) dissolved in 40.0 mL of ethyl acetate and 1.6 mL (5.96 mmol) of tributyl borate were added, and the mixture was stirred at 85° C. for 30 minutes, and then into the resultant mixture, 0.5 mL (5.04 mmol) of n-butylamine was added dropwise, then the temperature of the mixture was raised to 105° C., and the resultant mixture was stirred for 1.5 hours. Into the resultant mixture, 10 mL of 1N hydrochloric acid was added, and the mixture was stirred at 50° C. for 1 hour, and then the temperature of the mixture was returned to room temperature, the resultant mixture was subjected to extraction twice with ethyl acetate, an organic layer was combined together, and the resultant mixture was washed with brine and dried with Na$_2$SO$_4$, and the solvent was distilled off under reduced pressure. The obtained residue was purified with NH—SiO$_2$ (CHROMATOREX, manufactured by FUJI SILYSIACHEMICAL LTD.) open column chromatography (MeOH/CHCl$_3$=1:30), and 1.31 g (39%) of a compound d was obtained.

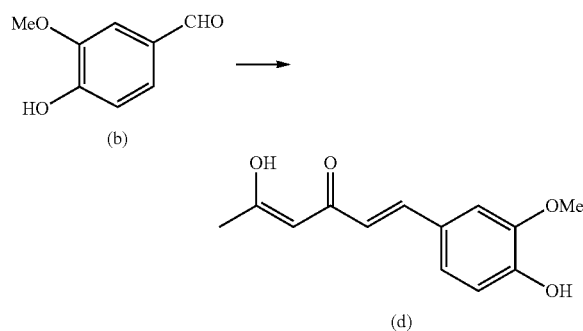

(3) 483.0 mg (2.06 mmol) of the compound d and 214.9 mg (3.08 mmol) of diboron trioxide were dissolved in 5.0 mL of ethyl acetate, and the resultant mixture was stirred at 85° C. for 30 minutes. Into this resultant mixture, 805.0 mg (1.72 mmol) of the compound c dissolved in 10.0 mL of ethyl acetate and 0.82 mL (3.05 mmol) of tributyl borate were added, and the mixture was stirred at 85° C. for 1 hour, and then into the resultant mixture, 71 μL (0.72 mmol) of piperidine was added dropwise, and the mixture was further stirred for 30 minutes. Into the resultant mixture, 7.0 mL of 0.5 N hydrochloric acid was added, and the mixture was stirred at 50° C. for 1 hour, and then the temperature of the mixture was returned to room temperature, and the resultant mixture was subjected to extraction twice with ethyl acetate, an organic layer was combined together, and the resultant mixture was washed with brine and dried with Na$_2$SO$_4$, and the solvent was distilled off under reduced pressure. The obtained residue was purified with SiO$_2$ flash column chromatography (AcOEt/n-hexane=60:40), and 917.7 mg (78%) of a compound e was obtained.

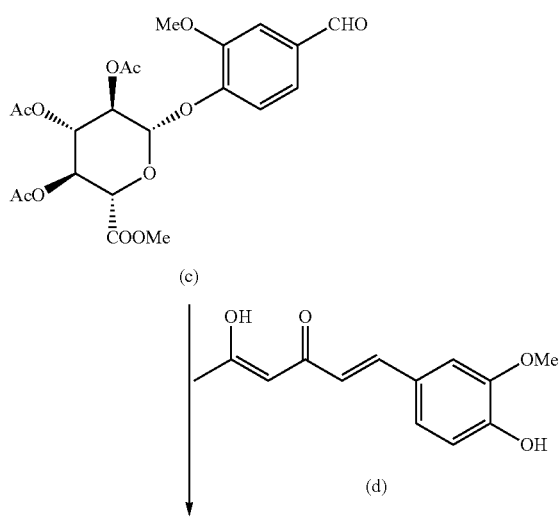

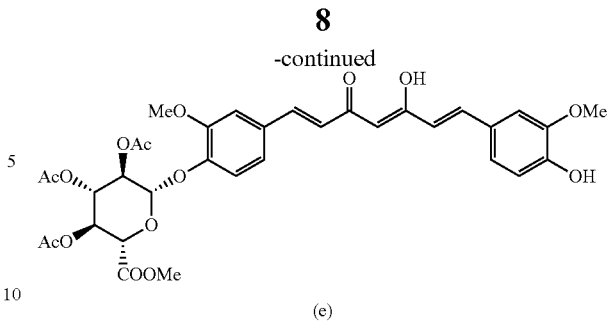

(4) In 24.5 mL of methanol, 875.1 mg (1.29 mmol) of the compound e was dissolved, and into the resultant mixture, 24.5 mL of a 1 N aqueous sodium hydroxide solution was added dropwise while cooling in ice, and the mixture was stirred at 50° C. for 1 hour. The pH was adjusted to be 3 to 4 by using 50% formic acid, and the precipitated solid was collected by filtration. The obtained solid was purified with HPLC (PEGASIL ODS SP100, φ20×250 mm, eluent: CH$_3$CN/H$_2$O=45:55, 0.1% TFA), and 253.1 mg (36%) of curcumin monoglucuronide (compound f) was obtained.

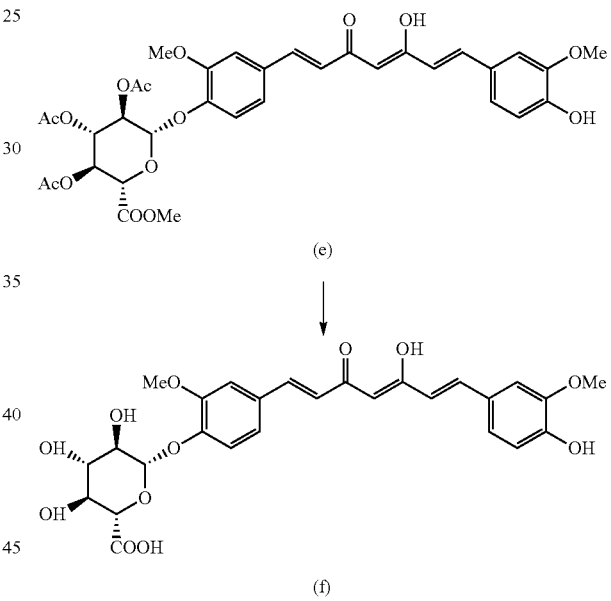

Test Example 1

(Intravenous Administration Test)
(1) Test Animals

As the test animals, 9-week old SD rats (male, with a body weight of 330 to 360 g, CHARLES RIVER LABORATORIES JAPAN, INC.) were used.
(2) Intravenous Administration Method The intravenous administration was performed as follows: a predetermined amount of the curcumin monoglucuronide prepared in Production Example 1 was dissolved into water for injection so as to be 30 mg/kg; and the obtained preparation was administered intravenously to each of the test animals (n=5) fasted for 12 hours or more before the administration via an indwelling catheter in the femoral artery of each of the test animals. In this regard, the catheter was indwelled in the femoral artery under isoflurane anesthesia on the day of administration and blood collection.

(3) Method for Collecting Blood and Plasma

Blood was collected via a catheter from the femoral artery of each of test animals by using a heparin-treated syringe under the restraint condition in a Ballman cage without anesthesia. In this regard, around 0.6 mL of blood was collected after each lapse of 1, 3, 5, 10, 15, 30, 60, 120, 240 and 480 minutes from the start of intravenous administration, and the collected blood was centrifuged (at 3,000 rpm, for 10 minutes, at 4° C.) to obtain the plasma.

(4) Fractional Determination of Concentration of Curcumin Conjugate and Free Curcumin in Plasma The concentration of each of the curcumin conjugate and free curcumin in plasma was determined by the following methods.

a. Pretreatment

Into 20 µL of the collected plasma, 100 µL of a 0.1M acetate buffer solution (pH 5.0) and 10 µL of a β-glucuronidase solution (around 68,000 units/mL) or distilled water were added, and the resultant mixture was kept at 37° C. for 1 hour, and then into the resultant mixture, 10 µL of 50% (v/v) methanol containing 20 ng/mL of mepronil, which was an internal standard liquid, was added. Next, into the mixture, 0.5 mL of chloroform was added, and the resultant mixture was stirred for 1 minute with a vortex mixer, then the mixture was treated for 15 minutes by using an ultrasonic generator, and the treated mixture was fractionated into a chloroform layer and a water layer by centrifugation (13,000×g, for 5 minutes, at room temperature). Further, this fractionation process was repeated twice. After that, the chloroform layer was collected, and dried and solidified by distilling off the solvent with a vacuum centrifugal concentrator, and to the dried and solidified matter, 100 µL of 50% (v/v) methanol was added, and then the resultant mixture was centrifuged (13,000×g, for 5 minutes, at room temperature) to collect a supernatant liquid.

In this regard, in the following test, a supernatant liquid prepared by using a β-glucuronidase solution was used as an enzyme-treated sample, and a supernatant liquid prepared by using distilled water in place of the β-glucuronidase solution was used as a non-enzyme-treated sample.

b. Measurement Method

By analyzing 2 µL of the enzyme-treated or non-enzyme-treated sample prepared in the above-described "a. Pretreatment" using LC-MS/MS (manufactured by Shimadzu Corporation), the concentration of each of the curcumin conjugate and free curcumin in plasma was determined.

That is, by measuring the concentration of the curcumin contained in the enzyme-treated sample that had been obtained by the treatment with β-glucuronidase, the total concentration of curcumin in plasma was measured.

On the other hand, by measuring the concentration of the curcumin in the non-enzyme-treated sample that had not been treated with β-glucuronidase, the concentration of free curcumin in plasma was measured.

Further, by subtracting the concentration of free curcumin from the total concentration of curcumin, the concentration of the curcumin conjugates contained in plasma was calculated.

In this regard, the LC-MS/MS analysis conditions were set to be a LC column of Atlantis T3 (2.1×150 mm, 3 µm, manufactured by Waters), a column temperature of 40° C., a flow rate of 0.2 mL/min, and a mobile phase of A of a 0.1% formic acid aqueous solution and B of 0.1% formic acid/acetonitrile, and the gradient elution was performed under the following conditions (Table 1). In addition, the MS analysis conditions were set to be an ionization mode of Electron Spray thermo ionization (ESI), Positive, a measurement mode of Multiple Reaction Monitoring (MRM), curcumin of 369.1→177.2 (m/z), and mepronil of 270→119 (m/z), and the evaluation was performed.

Further, the calibration curve used for quantifying curcumin was prepared with the measurement under the conditions similar to those described above by using various kinds of standard solutions (curcumin concentration of 0.9 to 225 ng/mL), which had been prepared by adding 10 µL of a 50% ethanol solution containing 20 ng/mL of mepronil into 90 µL of a 50% (v/v) methanol solution (curcumin standard solution) containing the curcumin in each amount of 1.0, 2.0, 3.9, 7.8, 15.6, 31.3, 62.5, 125 and 250 ng/mL.

TABLE 1

| * Gradient elution conditions | | | | | |
|---|---|---|---|---|---|
| | Time (min) | | | | |
| | 0 | 1.8 | 7 | 7.01 | 15 |
| A (%) | 40 | 5 | 5 | 40 | 40 |
| B (%) | 60 | 95 | 95 | 60 | 60 |

(5) Results

Concentration of each of the curcumin conjugates and free curcumin in plasma in a case where the curcumin conjugates had been administered intravenously was examined (FIG. 1).

The concentration of curcumin conjugates in plasma was 160492±19156 ng/mL after the lapse of 1 minute from the intravenous administration, 77803±6442 ng/mL after the lapse of 3 minutes from the intravenous administration, 80489±7161 ng/mL after the lapse of 5 minutes from the intravenous administration, 46853±10700 ng/mL after the lapse of 10 minutes from the intravenous administration, 22918±5271 ng/mL after the lapse of 15 minutes from the intravenous administration, 10191±3502 ng/mL after the lapse of 30 minutes from the intravenous administration, 4363±1354 ng/mL after the lapse of 1 hour from the intravenous administration, 1493±371 ng/mL after the lapse of 2 hours from the intravenous administration, 403±120 ng/mL after the lapse of 4 hours from the intravenous administration, and 78±39 ng/mL after the lapse of 8 hours from the administration, and was reduced with the passage of time. In addition, at this time, AUC 0.02-8 h (ng·h/mL) was 28387±5093 ng/mL, and Cmax (ng/mL) was 160492±19156 ng/mL.

On the other hand, it was found that the concentration of free curcumin in plasma was not observed before the intravenous administration of curcumin conjugates, however, was 10143±3832 ng/mL after the lapse of 1 minute from the intravenous administration of curcumin conjugates, and the free curcumin were present at a high concentration in plasma. In addition, it was found that the concentration of free curcumin in plasma was 7562±2903 ng/mL after the lapse of 3 minutes from the intravenous administration, 5707±2539 ng/mL after the lapse of 5 minutes from the intravenous administration, 3596±1233 ng/mL after the lapse of 10 minutes from the intravenous administration, 2764±796 ng/mL after the lapse of 15 minutes from the intravenous administration, 1605±592 ng/mL after the lapse of 30 minutes from the intravenous administration, 568±197 ng/mL after the lapse of 1 hour from the intravenous administration, 117±39 ng/mL after the lapse of 2 hours from the intravenous administration, 16±5 ng/mL after the lapse of 4 hours from the intravenous administration, and 6±14 ng/mL after the lapse of 8 hours from the intravenous administration, and the free curcumin was maintained at a high concentration in plasma for a long period of time. In addition, at this time, AUC 0.02-8 h (ng·h/mL) was 2778±962 ng/mL, and Cmax (ng/mL) was 10143±3832 ng/mL.

As described above, it was found that by administering curcumin conjugates parenterally, the concentration of free curcumin having a pharmacological action in blood can be maintained at a high level over a long period of time.

Test Example 2

(Anti-Tumor Effect by Intravenous Administration of Curcumin Conjugates in Various Doses)
(1) Test Animals As the test animals, 5-week old BALB/cAnNcr j-nu/nu (homo) mice (female, with a body weight of around 15 to 19 g, CHARLES RIVER LABORATORIES JAPAN, INC.), which had been purchased and acclimated to the environment for around 10 days, was used.
(2) Transplantation Method $1 \times 10^7$ or $4 \times 10^6$ colorectal cancer cells derived from adult human male colon HCT116 (ATCC No. CCL-247) were transplanted subcutaneously into the flank of each of the test animals by using a 27 G injection needle.
(3) Administration Method Into each of the mice (n=5 or 8) inoculated with the cancer cells (HCT116), after each lapse of 0, 2, 4, 6 and 8 days from the start of inoculation or after each lapse of 0, 3, 5, 7, 10, 12, 14, 17, 19 and 21 days from the start of inoculation, 150 to 230 μL of the injection prepared by dissolving the curcumin monoglucuronide that had been prepared in the above-described Production Example 1 into water for injection (prepared so that curcumin monoglucuronide was administered in an amount of 30 mg or 90 mg per kg body weight) was administered intravenously by using an injection needle, and further the tumor size of each of the mice was examined with the passage of days. In this regard, in the control group, mice to which water for injection excluding curcumin monoglucuronide had been administered intravenously were used.
(4) Evaluation of Tumor Size For the tumor size, after each lapse of 0, 4, 7, 11 and 14 days from the start of administration or after each lapse of 0, 4, 7, 11, 14, 18 and 21 days from the start of administration, the length, width and height of the tumor were measured by using a vernier caliper, and the tumor size was calculated by the following equation.

Tumor size (mm$^3$)=length×width×height×0.5

(5) Concentration of Curcumin Conjugates and Free Curcumin in Tumor Tissue

For the mice (n=8) inoculated with the $4 \times 10^6$ cancer cells (HCT116), the tumor after the lapse of 2 hours from the intravenous administration of curcumin monoglucuronide (90 mg/kg) after the lapse of 21 days from the start of inoculation was removed from each of the mice, the removed tumor was rinsed with a saline solution, and then immediately frozen in liquid nitrogen, and the frozen tumor was stored in an ultra-low temperature tank at −80° C.

The frozen and stored tumor was thawed while cooling in ice, an adequate amount of a saline solution was added to the thawed tumor, and the thus obtained tumor was homogenized with a glass homogenizer, the concentration of each of the curcumin conjugates and free curcumin in the pulverized tumor obtained as described above were measured to examine the concentration of each of the curcumin conjugates and free curcumin contained in the tumor tissue.
(6) Results
(Dose of 30 mg/kg—in Case of Mouse)

Figure 2:
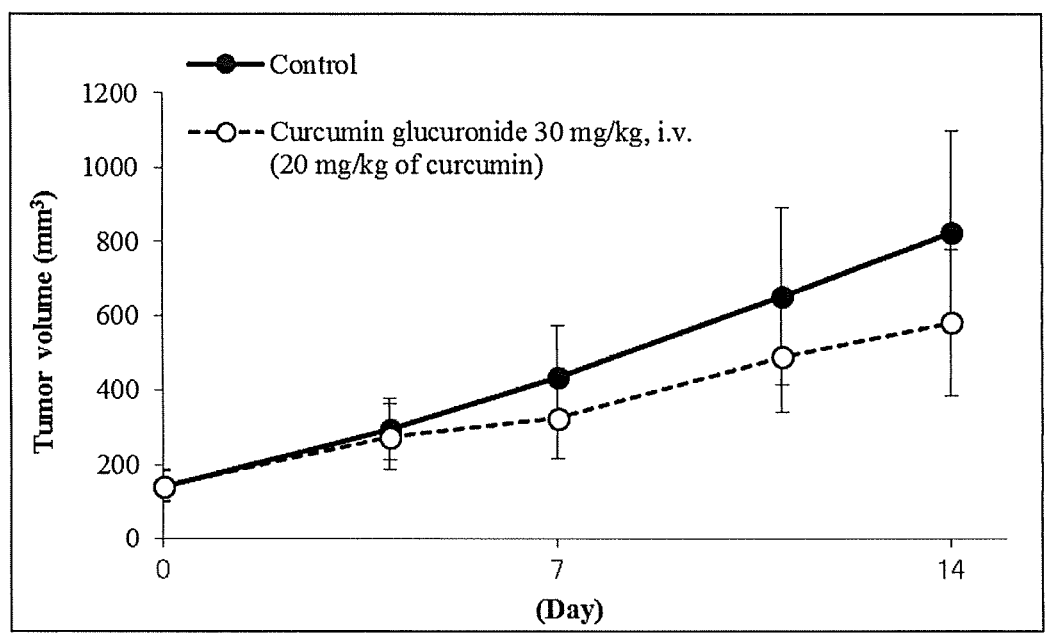
FIG. 2 shows the anti-tumor effect of curcumin conjugates (30 mg/kg) by intravenous administration.

The anti-tumor effect was examined in a case where 30 mg of curcumin conjugates (curcumin monoglucuronide) per kg body weight of a mouse was administered parenterally (FIG. 2).

In a case where curcumin conjugates (curcumin monoglucuronide) were administered parenterally (30 mg/kg—mouse), the tumor size was 142.9±45.5 mm$^3$ after the lapse of 0 day from the start of administration, 275.1±88.1 mm$^3$ after the lapse of 4 days from the start of administration, 326.1±110 0.7 mm$^3$ after the lapse of 7 days from the start of administration, 489.4±147.8 mm$^3$ after the lapse of 11 days from the start of administration, and 581.2±197.4 mm$^3$ after the lapse of 14 days from the start of administration.

On the other hand, in a case of the control group, the tumor size was 142.5±39.9 mm$^3$ after the lapse of 0 day from the start of administration, 297.0±82.9 mm$^3$ after the lapse of 4 days from the start of administration, 435.1±138.6 mm$^3$ after the lapse of 7 days from the start of administration, 653.3±239.7 mm$^3$ after the lapse of 11 days from the start of administration, and 825.9±271.3 mm$^3$ after the lapse of 14 days from the start of administration, and showed larger values at any time as compared to those in the case where the curcumin conjugates (curcumin monoglucuronide) had been administered parenterally.

In addition, when the biochemical test using the serum obtained by the blood collection after the lapse of 14 days from the start of administration was referred to Oriental Yeast Co., Ltd. (biochemical test set (liver and biliary diseases set), 21 items), no abnormality was found in the test values.
(Dose of 90 mg/kg—in Case of Mouse)

Figure 3:
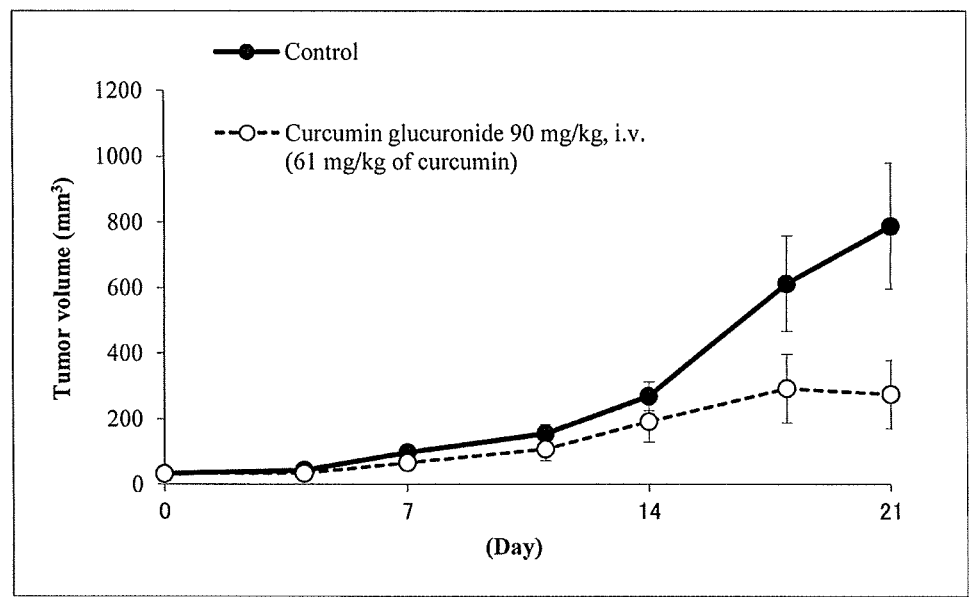
FIG. 3 shows the anti-tumor effect of curcumin conjugates (90 mg/kg) by intravenous administration.

The anti-tumor effect was examined in a case where 90 mg of curcumin conjugates (curcumin monoglucuronide) per kg body weight of a mouse was administered parenterally (FIG. 3).

In a case where curcumin conjugates (curcumin monoglucuronide) were administered parenterally (90 mg/kg—mouse), the tumor size was 17.4±3.2 mm$^3$ after the lapse of 0 day from the start of administration, 23.6±8.4 mm$^3$ after the lapse of 4 days from the start of administration, 42.6±16.6 mm$^3$ after the lapse of 7 days from the start of administration, 77.5±28.9 mm$^3$ after the lapse of 11 days from the start of administration, 122.9±42.6 mm$^3$ after the lapse of 14 days from the start of administration, 204.4±76.2 mm$^3$ after the lapse of 18 days from the start of administration, and 190.2±70.1 mm$^3$ after the lapse of 21 days from the start of administration.

On the other hand, in a case of the control group, the tumor size was 17.6±2.9 mm$^3$ after the lapse of 0 day from the start of administration, 29.7±5.9 mm$^3$ after the lapse of 4 days from the start of administration, 61.8±14.9 mm$^3$ after the lapse of 7 days from the start of administration, 106.3±22.0 mm$^3$ after the lapse of 11 days from the start of administration, 179.8±29.5 mm$^3$ after the lapse of 14 days from the start of administration, 376.4±81.7=$^3$ after the lapse of 18 days from the start of administration, and 505.6±100.4 mm$^3$ after the lapse of 21 days from the start of administration, and showed larger values at any time as compared to those in the case where the curcumin conjugates (curcumin monoglucuronide) had been administered parenterally.

In addition, when the concentration of each of the curcumin conjugates and free curcumin contained in the tumor tissue was examined, the concentration of the curcumin conjugates in the tumor tissue was 605.4±465.5 ng/g, and the concentration of the free curcumin in the tumor tissue was 1464.5±840.9 ng/g.

From these results, it was found that the curcumin conjugates exerted the effect of significantly suppressing the tumor growth by being administered parenterally. Further, it was observed that free curcumin having a pharmacological action was present in the tumor at a high concentration, and the tumor growth inhibitory effect was presumed to be due to the free curcumin.

Test Example 3

(Single Dose Toxicity Test)

Intravenous administration of a single dose of curcumin monoglucuronide was performed to each of the mice at each dose of 125, 250, 500 and 1000 mg/kg, and the toxicity thereof was evaluated. In this regard, the number of mice in each group was set to be n=5.
(1) Test Animals As the test animals, 6-week old Slc:ICR mice (male, with a body weight of 27 to 31 g, Japan SLC, Inc.), which had been purchased and acclimated to the environment for around 6 days, was used.
(2) Administration Method 320 to 370 µL of the solution prepared by dissolving the curcumin monoglucuronide prepared in the above-described Production Example 1 into a saline solution (in cases of 125, 250 and 500 mg/kg) or water for injection (in a case of 1000 mg/kg) (solution being prepared so that curcumin monoglucuronide was administered in an amount of 125 mg, 250 mg, 500 mg or 1000 mg per kg body weight) was administered intravenously to each of the mice (n=5) by using an injection needle.
(3) State Observation Observation of the state of each of the mice was performed by recording the type, extent, expression time, recovery time, and death (death detection) time of all of the toxic signs observed macroscopically.
(4) Observation Time Observation was performed at a time immediately after administration, at a time after each lapse of 30 minutes, 1, 2, 4 and 6 hours from the start of administration, and once a day from the day following the date of administration (up to after the lapse of 14 days from the start of administration). In this regard, in the 1000-mg/kg administration group, acute symptoms were observed immediately after administration, and therefore, observation was frequently performed up to after the lapse of 1 hour from the start of administration.
(5) Measurement of Body Weight The body weight was measured by using an electronic balance (UW4200S, Shimadzu Corporation) immediately before administration, and after each lapse of 1, 3, 7, 10 and 14 days from the administration.
(6) Blood Biochemical Test Blood biochemical test was performed by the following method. That is, mice were fasted for 4 hours or more after the end of the mouse observation period (after the lapse of 14 days from the start of administration), the fasted mice were subjected to laparotomy under anesthesia by intraperitoneal administration of pentobarbital sodium, and the blood was collected from the abdominal aorta (the amount of the blood was 0.6 mL or more). Next, the collected blood was anti-coagulated with heparin sodium, and then the anti-coagulated blood was centrifuged (4° C., 3000 rpm, for 10 minutes) to obtain the plasma, and transaminase (AST and ALT) contained in the plasma was measured.
(7) Autopsy Method After the end of the observation period (after the lapse of 14 days from the start of administration), autopsy was performed as follows: blood was collected from each of the mice under anesthesia with pentobarbital sodium; and then the mice were sacrificed by exsanguination by cutting the abdominal aorta and the caudal vena; each of the sacrificed mice was dissected according to a pathological technique; and the cranium, the intrathoracic organs, the intraperitoneal organs, and the tissues thereof were observed macroscopically.
(8) Results
(State of Mouse by Macroscopy)

With regard to the state of a mouse in each administration group, in the 125-mg/kg administration group, no abnormality was found in the states of all of the mice (n=5) throughout the observation period.

In the 250-mg/kg administration group, piloerection was observed in 1 case (n=1) after the lapse of 1 hour from the start of administration, however, the mouse in this case was recovered later.

In the 500-mg/kg administration group, reduction of locomotor activity was observed in all of the mice (n=5) from immediately after administration to after the lapse of 4 hours from the administration, loose stools were observed in all of the cases (n=5) from after the lapse of 30 minutes to 1 hour from the start of administration, and piloerection was observed in 3 cases (n=3) from after the lapse of 30 minutes to 4 hours from the start of administration, however, all of the symptoms were recovered later.

In the 1000-mg/kg administration group, prone position and reduction of locomotor activity were observed in all of the mice (n=5) from immediately after administration to after the lapse of 30 minutes from the start of administration. In addition, bradypnea was observed in 2 cases (n=2) immediately after administration and in 1 case (n=1) after the lapse of 30 minutes from the start of administration. Further, dyspnea was observed in 2 cases (n=2) within 30 minutes from the start of administration. Furthermore, paralytic gait was observed in 2 cases (n=2) within 30 minutes from the start of administration and in 1 case (n=1) from after the lapse of 30 minutes to 1 hour from the start of administration. Moreover, death was observed in 4 cases (n=4) within 30 minutes from the start of administration and in 1 case (n=1) from after the lapse of 30 minutes to 1 hour from the start of administration.

From these results, it was found to be safe at a single dose of 500 mg/kg or less, and found that 50% lethal dose ($LD_{50}$) was between 500 mg/kg and 1000 mg/kg.
(Changes in Body Weight)

Figure 4:
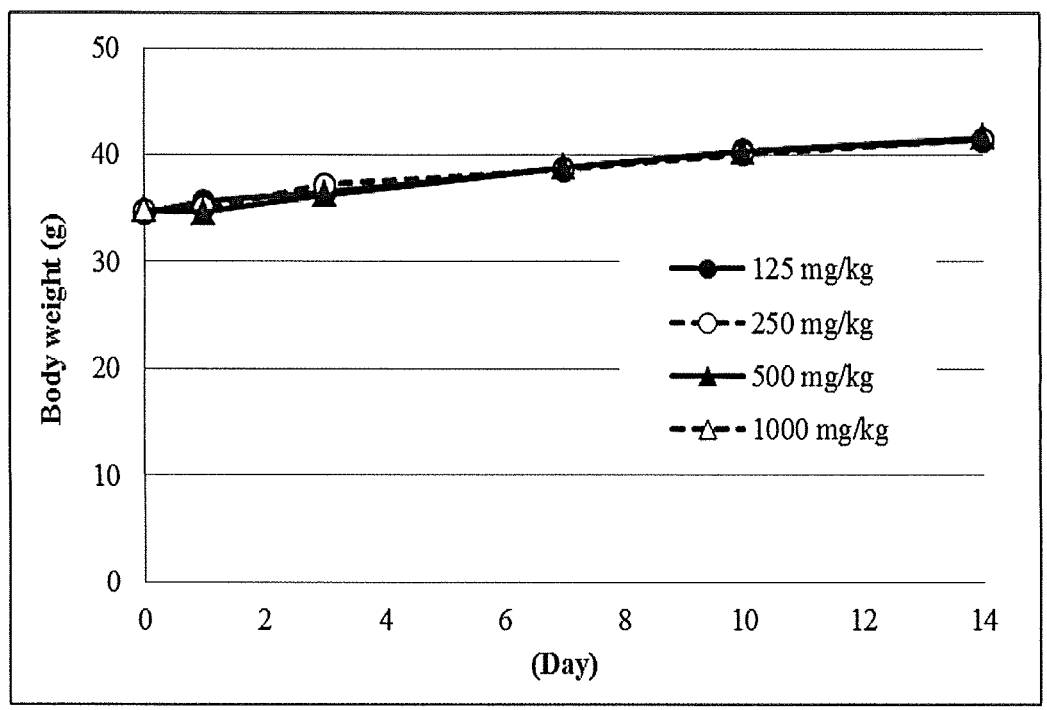
FIG. 4 shows the influence of single dose of curcumin conjugates on the body weight.

Changes in the body weight of a mouse in each group are shown in FIG. 4. In the 125-mg/kg administration group, all of the animals showed a steady weight gain up to after the lapse of 14 days from the start of administration. Slight weight loss was observed in 1 case (n=1) after the lapse of 1 day from the start of administration in the 250-mg/kg administration group and in 3 cases (n=3) after the lapse of 1 day from the start of administration in the 500-mg/kg administration group, however, all of the animals showed a steady weight gain up to after the lapse of 14 days from the start of administration.
(Blood Biochemical Test)

For the blood biochemical test of a mouse in each group (125-, 250- and 500-mg/kg administration groups), the AST levels in the 125-, 250- and 500-mg/kg administration groups were 37±4, 34±3 and 37±3 IU/L, respectively, and the ALT levels in the 125-, 250- and 500-mg/kg administration groups were 24±6, 25±4 and 34±5 IU/L, respectively, and which showed normal levels, respectively. In this regard, the test was not conducted in the 1000-mg/kg administration group because all of the mice died.
(Autopsy)

When autopsy was performed in each group (125-, 250- and 500-mg/kg administration groups), no abnormality was found in all of the administration groups. In this regard, the autopsy was not performed in the 1000-mg/kg administration group because all of the mice died.

From these results, it was found to be safe at a single dose of up to 500 mg/kg without finding any abnormalities.

Test Example 4

(Deconjugation of Curcumin Diglucuronide with β-Glucuronidase)

It was examined whether or not curcumin diglucuronide (manufactured by SynInnova Laboratories Inc.) was deconjugated with β-glucuronidase. In this regard, as a control, curcumin monoglucuronide was used for the examination.
(1) Test Sample As the curcumin monoglucuronide, curcumin monoglucuronide prepared in the above-described Production Example 1 was used. In addition, as the curcumin diglucuronide, commercially available curcumin diglucuronide (manufactured by SynInnova Laboratories Inc.) was used.
(2) Pretreatment Into 100 μL of a 0.1 M acetate buffer solution (pH 5.0) and 10 μL of a β-glucuronidase solution (around 68,000 units/mL), 10 μL of curcumin monoglucuronide (2.81 μg/mL, n=3) or 10 μL of curcumin diglucuronide (2.45 μg/mL, n=3) was added, and the resultant mixture was kept at 37° C. for 1 hour, and into this mixture, 10 μL of 50% (v/v) methanol containing 20 ng/mL of mepronil, which was an internal standard liquid, was added. Next, into the resultant mixture, 0.5 mL of chloroform was added, and the mixture was stirred for 1 minute with a vortex mixer, and then the stirred mixture was treated for 15 minutes by using an ultrasonic generator, and the treated mixture was fractionated into a chloroform layer and a water layer by centrifugation (10,000×g, for 5 minutes, at room temperature). Further, this fractionation process was repeated twice. After that, the chloroform layer was collected, and dried and solidified by distilling off the solvent with a vacuum centrifugal concentrator, and to the dried and solidified matter, 100 μL of 50% (v/v) methanol was added, and then the resultant mixture was centrifuged (10,000×g, for 5 minutes, at room temperature) to collect a supernatant liquid, and the collected supernatant liquid was taken as an enzyme-treated sample.
(3) Measurement Method In 2 μL of the enzyme-treated sample prepared in the above (2), free curcumin was measured by the method described in "b. Measurement method" in (4) in Test Example 1.

In this regard, the calibration curve used for quantifying curcumin was prepared with the measurement under the conditions similar to those described above by using a supernatant liquid (curcumin concentration of 4.1 to 261.5 ng/mL), which had been prepared as follows: into 100 μL of a 0.1 M acetate buffer solution (pH 5.0) and 10 μL of a β-glucuronidase solution (around 68,000 units/mL), 100 μL of a 50% (v/v) methanol solution (curcumin standard solution) containing the curcumin in each amount of 4.1, 16.3, 65.4 and 261.5 ng/mL and 10 μL of a 50% ethanol solution containing 20 ng/mL of mepronil were added; and the resultant mixture was subjected to the treatment by chloroform and the solvent removal by distillation with a vacuum centrifugal concentrator in a similar manner as in the above (2); then into this mixture, 100 μL of 50% (v/v) methanol was added; and then the resultant mixture was centrifuged (10,000×g, for 5 minutes, at room temperature) to obtain the supernatant liquid.
(4) Results The concentration of the curcumin contained in the enzyme-treated sample, which had been obtained by enzymatically treating curcumin monoglucuronide with β-glucuronidase, was 159.1±6.1 ng/mL.

On the other hand, the concentration of the curcumin contained in the enzyme-treated sample, which had been obtained by treating curcumin diglucuronide with β-glucuronidase, was 82.4±0.8 ng/mL.

From the results described above, similar to the curcumin monoglucuronide, free curcumin was also observed by treating the curcumin diglucuronide with β-glucuronidase, and therefore it was found that the curcumin diglucuronide was deconjugated with β-glucuronidase. For this reason, it is considered that even in a case where curcumin diglucuronide is administered parenterally, the effect similar to that of curcumin monoglucuronide can be obtained.

The invention claimed is:

1. A method of administering curcumin to a subject to maintain a pharmacological concentration of free curcumin in the subject's blood, comprising intravenously administering an aqueous solution comprising curcumin monoglucuronide wherein the concentration of free curcumin in the blood achieved thru IV administration is greater than the that achieved by oral administration of curcumin.

* * * * *